United States Patent [19]
Flaherty

[11] Patent Number: 5,702,363
[45] Date of Patent: Dec. 30, 1997

[54] SEPTUMLESS IMPLANTABLE TREATMENT MATERIAL DEVICE

[76] Inventor: J. Christopher Flaherty, 242 Ipswich Rd., Topsfield, Mass. 01983

[21] Appl. No.: 475,773

[22] Filed: Jun. 7, 1995

[51] Int. Cl.⁶ ................................................. A61M 11/00
[52] U.S. Cl. ........................................... 604/93; 604/175
[58] Field of Search ........................ 604/93, 167–175, 604/82–86, 241, 242, 243, 283

[56] References Cited

U.S. PATENT DOCUMENTS

| | | |
|---|---|---|
| 3,951,147 | 4/1976 | Tucker et al. . |
| 4,496,343 | 1/1985 | Prosl et al. . |
| 4,573,994 | 3/1986 | Fischell et al. . |
| 4,645,495 | 2/1987 | Vaillancourt . |
| 4,654,033 | 3/1987 | Lapeyre et al. . |
| 5,053,013 | 10/1991 | Ensminger et al. . |
| 5,057,084 | 10/1991 | Ensminger et al. . |
| 5,137,529 | 8/1992 | Watson et al. . |
| 5,180,365 | 1/1993 | Ensminger et al. . |
| 5,185,003 | 2/1993 | Brethauer . |
| 5,228,879 | 7/1993 | Ensminger et al. . |
| 5,263,930 | 11/1993 | Ensminger . |
| 5,281,199 | 1/1994 | Ensminger et al. . |
| 5,306,255 | 4/1994 | Haindl . |
| 5,308,336 | 5/1994 | Hart et al. . |
| 5,324,270 | 6/1994 | Kayan et al. . |
| 5,350,360 | 9/1994 | Ensminger et al. . |
| 5,356,381 | 10/1994 | Ensminger et al. . |

FOREIGN PATENT DOCUMENTS

| | | |
|---|---|---|
| 110117 | 6/1984 | European Pat. Off. . |
| 0 159 260 | 10/1985 | European Pat. Off. . |
| 41 29 782 | 10/1992 | Germany . |
| WO 83/02063 | 6/1983 | WIPO . |
| WO 94/05246 | 3/1994 | WIPO . |
| WO 94/05351 | 3/1994 | WIPO . |
| WO94/05246 | 3/1994 | WIPO . |

OTHER PUBLICATIONS

PORT–A–CATH® Epidural Implantable Access System Instructions for Use, ©1991 Pharmacia Deltec Inc., St. Paul, MN 55112.

PORT–A–CATH® Epidural Implantable Access System, Patient Information, ©1991 Pharmacia Deltec Inc., St. Paul, MN 55112.

PORT–A–CATH® Implantable Epidural Access System, Journal Ad, ©1991 Pharmacia Deltec Inc., St. Paul, MN 55112.

CELSA–LG, Detail Aid, Avenue des Temps Modernes, France.

*Primary Examiner*—John D. Yasko

[57] ABSTRACT

A septumless implantable access device suitable for delivering a liquid medication to a site remote from the site of port implantation is disclosed, which contains a filter assembly for removing particulate material from fluid injected into the port. The filter assembly of the invention contains a first reservoir chamber having cutouts, recesses, and/or sharp corners in which particulate material may be trapped, and additionally having a first wall forming a filter barrier capable of 360° of fluid flow therethrough. The implantable access device may also include an infusion pump apparatus coupled to the access device.

18 Claims, 3 Drawing Sheets

SEPTUMLESS IMPLANTABLE TREATMENT MATERIAL DEVICE

The present invention relates to implantable reservoirs for providing a treatment material, such as a drug in fluid form, directly to an internal site of a patient. More specifically, the invention relates to a septumless implantable reservoir containing a filtering means to remove particulate matter and bacteria from fluid injected into the reservoir.

BACKGROUND OF THE INVENTION

Implantable devices have been developed for infusion or delivery of medications into a specific body site, for example, to avoid repeated intravenous, intrathecal, or epidural injections and thereby to minimize discomfort to a patient. Such devices generally include a housing containing an internal reservoir or chamber with an outlet cannula for connection to a catheter, and a penetrable resealable septum, all of which are biocompatible. The devices may be implanted subcutaneously, with the septum oriented just under the skin to provide easy access to repeated needle penetration. A catheter generally connects the outlet cannula of the device to a site remote from the site of implantation. Medication may be injected through the septum into the reservoir of the device, thus allowing delivery of the medication directly to the remote treatment site.

Some medical conditions require installation of a pump drug delivery device in the body of the patient which is capable of delivering medication into a remote site through a catheter over a prolonged period of time. For example, chronic pain patients may receive such a pump for delivery of analgesics directly into the central nervous system via the spinal fluid. Such an access device may also be installed to replenish medication supply to a pump drug delivery device.

Conventional intraspinal access devices are generally similar to other implantable treatment reservoirs for injecting drugs or withdrawing blood samples, such as central venous access devices. All of those devices include a biocompatible housing containing an internal chamber or reservoir in fluid communication with the treatment site, i.e., the vascular system, intrathecal space, or epidural space, through a catheter, and a septum capable of resealing after being punctured by a needle. The useful life of implantable treatment material devices which include a septum is limited by the number of punctures that the septum can withstand before it leaks, because repeat access slowly degrades the silicone until ultimately it is unable to resist the passage of fluids or other elements that are in communication with the device. Moreover, expensive non-coring needles or filaments are preferably used to access the device, in order to reduce the damage to the septum. Such non-coring filaments are also preferably of small diameter or gauge, rendering septum-containing devices unsuitable for treatments which require high blood flows.

Intraspinal access devices of the prior art may develop blockages from particulate matter such as metal flings from needles and other metal present or from parts of the septum which may slough off as a result of needle puncture. Presently available intraspinal access devices and systems include filters which may be between the syringe and the needle or in the device itself.

Several kinds of filters are currently available. One kind, for access devices having a generally cylindrical internal reservoir with the exit port extending from a point on the cylindrical side surface of the reservoir, comprises a cylindrical screen positioned in the reservoir and having a diameter substantially equal to the inner diameter of the reservoir. A second kind, for access devices having an exit port extending from a point on the bottom surface of the reservoir, includes a mesh screen positioned on the bottom surface of the reservoir. These kinds of intraspinal access device filters are not capable of screening out much particulate matter, because the mesh of such filters is necessarily large in order to accommodate a satisfactory flow rate. One problem with a finer mesh is that needles injected into the septum of the device would cause more significant damage to the screen. A second problem is that the screens are placed directly adjacent to the outlet port, allowing only a small area of the screen to permit flow-through of fluid from the device, i.e., and that small area of flow-through is easily clogged. Also the fluid impedance is relatively high for small area filters.

U.S. Pat. No. 5,137,529 discloses an injection device containing a filter barrier extending across the internal injection chamber and separating the injection chamber into an upper portion adjacent to the septum and a lower portion in open fluid communication with the outlet conduit of the device.

U.S. Pat. No. 5,185,003 discloses a device for injecting medicaments containing a circular cylindrical filter member having a conical inner wall and being exactly adapted to fit the diameter of the inner cavity of the port. Another embodiment disclosed in U.S. Pat. No. 5,185,003 includes a filter member in the form of a plane-parallel disc between the inner cavity of the port and the outlet opening to the catheter.

A need exists, therefore, for a septumless implantable treatment access device capable of filtering particulate matter out of medication being delivered to a specific body site.

One object of the invention is to provide a septumless implantable treatment access device which is capable of removing debris from fluid injected therein.

Another object of the invention is to provide a septumless intraspinal access device for intrathecal or epidural delivery of medications which are substantially free of particulate material.

SUMMARY OF THE INVENTION

The present invention provides a septumless multi-chambered implantable device including an access device having improved filtering capabilities. The implantable access device of the invention includes a biocompatible housing having at least one entry port and at least one aperture with a passageway extending therebetween. The housing further includes a valve assembly disposed in the passageway, and the valve assembly includes a valve and a sealing element. In use, a filament, such as a needle, is introduced through the entry port, activating (opening) the valve to allow access through the passageway. Independent of the activation of the valve, a seal is created about the filament by the sealing element before the valve opens. The aperture communicates with an internal substantially cylindrical reservoir in the housing, the reservoir being defined by a lateral surface extending about a central axis and a bottom surface. An outlet cannula defining an internal channel extending from a point on the internal wall of the reservoir extends from the housing and is adapted to receive a catheter. A filter assembly is disposed in the reservoir.

The filter assembly of the invention includes a toroidal fluid permeable first wall, preferably a substantially cylindrical shell interior to and spaced apart from the lateral surface of the reservoir. In one form, the diameter of the first wall is sufficiently smaller than the inner diameter of the reservoir to allow a full 360° of fluid flow through the first wall, effectively utilizing substantially all of the surface area of the first wall as a filter barrier, in contrast to the limited surface area of known injection device filters. Placement of the first wall establishes two chambers: a first annular chamber between the first wall and the lateral surface of the housing reservoir; and a first reservoir chamber interior to the first wall. The first annular chamber and the first reservoir chamber are in fluid communication only through the filter assembly's first wall, and the outlet cannula channel is in direct fluid communication only with the first annular chamber. In some embodiments, the filter assembly of the invention comprises a one-stage filter; for example, a one-stage filter is formed by filter assemblies having only a first wall. In other embodiments a substantially cylindrical, fluid permeable second wall may be provided to form a two-stage filter assembly, the second wall being placed interior to and spaced apart from the first filter assembly wall. The diameter of the second wall is sufficiently smaller than the diameter of the first wall to allow a full 360° of fluid flow through the second wall, allowing substantially all of the surface area of the second wall to be useful as a filter barrier. In these embodiments, the second wall forms an additional, second annular chamber within the first reservoir chamber.

In accordance with the present invention, fluid injected through the passageway into the filter assembly flows from the first reservoir chamber through the substantially cylindrical first wall, into the first annular chamber formed by the first wall of the filter assembly and the inner wall of the reservoir. Fluid then flows from the first annular chamber to the outlet cannula to the treatment site. In those embodiments having a second wall and second annular chamber, injected fluid flows from the first reservoir chamber through the second wall into the second annular chamber, through the first wall to the first annular chamber and thence to the outlet cannula channel. In accordance with the present invention, fluid has no direct access from the first reservoir chamber to the outlet cannula channel.

The implantable device of the invention functions to filter debris out of fluid injected therein. The invention uses fluid dynamics created by the shape of the walls of the first reservoir chamber to trap particles in specifically designed cutouts, recesses, and/or sharp corners. When the device is accessed by a filament and fluid is injected into the filter assembly, a fluid flow is established in the first reservoir chamber which promotes accumulation of particulate matter from the fluid into the cutouts, recesses, and/or sharp corners. The cutouts, recesses, and/or sharp corners create static areas of fluid flow (dead space) or eddy flow paths in which particulate material accumulates. In accordance with the invention, the configuration of the cutouts, recesses, and/or sharp corners of the first reservoir chamber may be varied to optimize entrapment of particulate material. Thus using the implantable treatment material device of the invention, mainly particulate-free material is delivered to the treatment site. The implantable device of the invention is especially suitable as an intraspinal access device for epidural or intrathecal administration of drugs.

In one embodiment, the invention provides an implantable access device comprising:

A. a biocompatible housing having at least one entry port and at least one aperture with a passageway extending therebetween, said entry port being adapted to receive a filament for passage into said passageway, said housing further including and disposed in said passageway a valve assembly comprising a valve and a sealing element, said valve assembly adapted to be activated by said filament after passage of said filament through said entry port whereupon a seal, independent of activation of said valve, is created by said sealing element about said filament before said valve opens to allow access through said passageway, said aperture communicating with an internal substantially cylindrical reservoir in the housing, said reservoir being defined by a lateral surface extending about a central axis and a bottom surface;

B. an outlet extending through said housing along an outlet channel axis from a point on said lateral surface of said reservoir; and C. a filter assembly disposed in said reservoir, said filter assembly including a substantially cylindrical fluid permeable first wall interior to and spaced apart from said lateral surface of said reservoir, said first wall establishing a first annular chamber between said first wall and said lateral surface and a first reservoir chamber interior to said first wall, said first annular chamber and said first reservoir chamber being in fluid communication only through said first wall, and said outlet being in direct fluid communication with said first annular chamber.

BRIEF DESCRIPTION OF THE DRAWINGS

The foregoing and other objects of this invention, the various features thereof, as well as the invention itself, may be more fully understood from the following description, when read together with the accompanying drawings in which.

In the various figures, corresponding elements are denoted by the same reference designations.

DESCRIPTION OF THE PREFERRED EMBODIMENTS

Figure 1A:
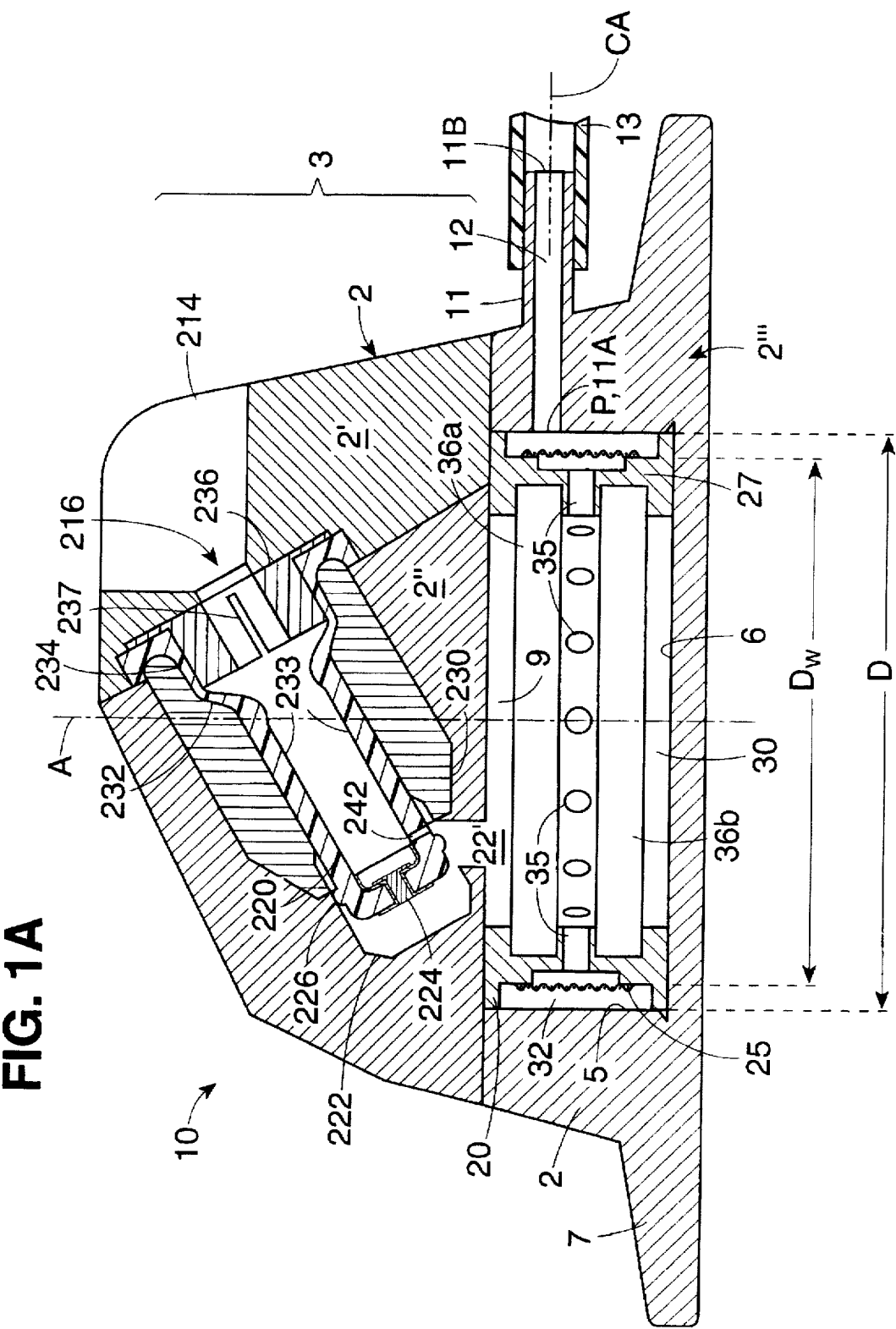
FIG. 1A shows in sectional schematic form, a septumless implantable two-stage filter access device of the invention with an internal reservoir and filter assembly with a valve embodiment comprising an opening, in the closed configuration.
Figure 1B:
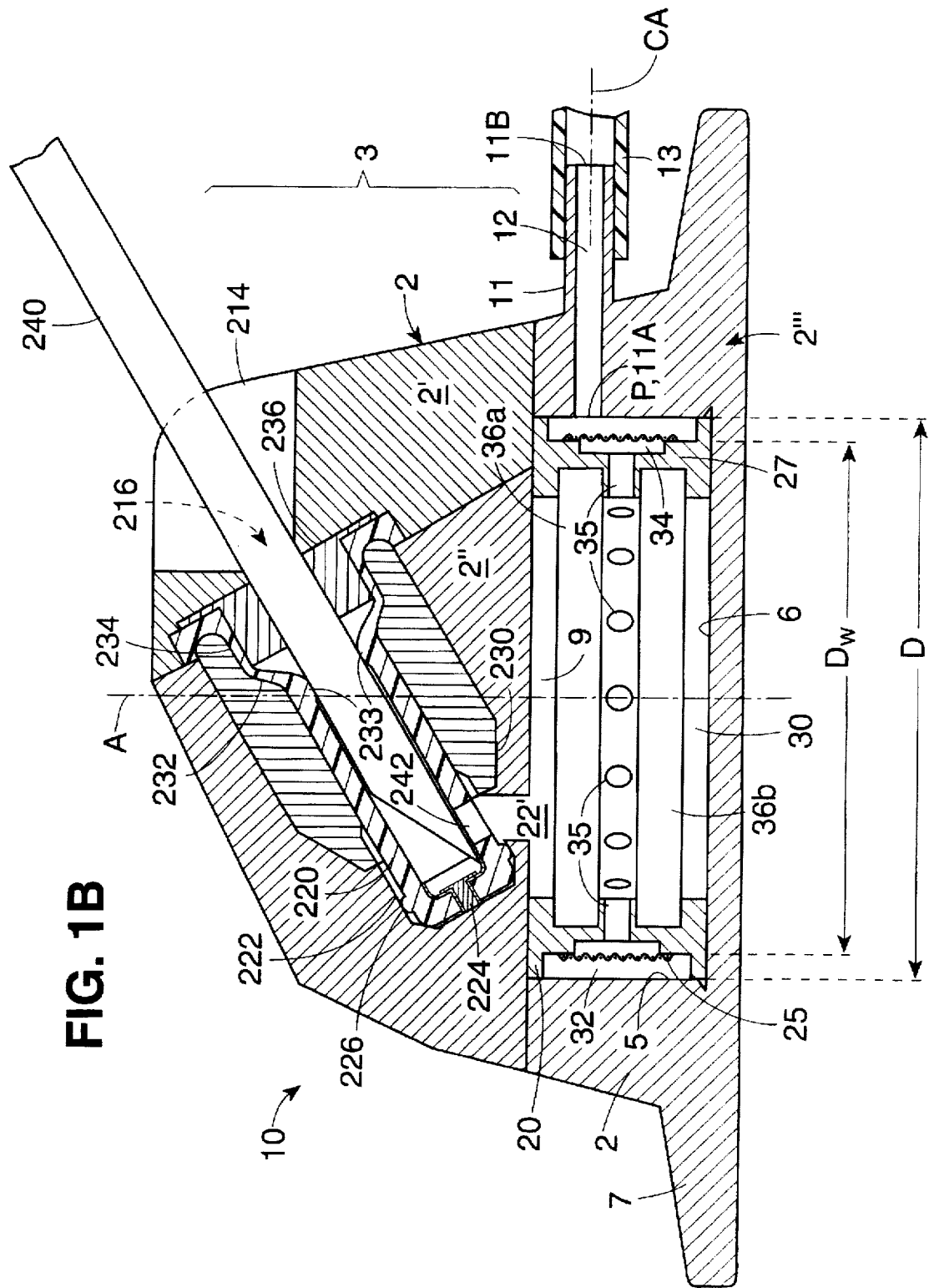
FIG. 1B shows in sectional schematic form, the device of FIG. 1A in an open configuration.
Figure 2:
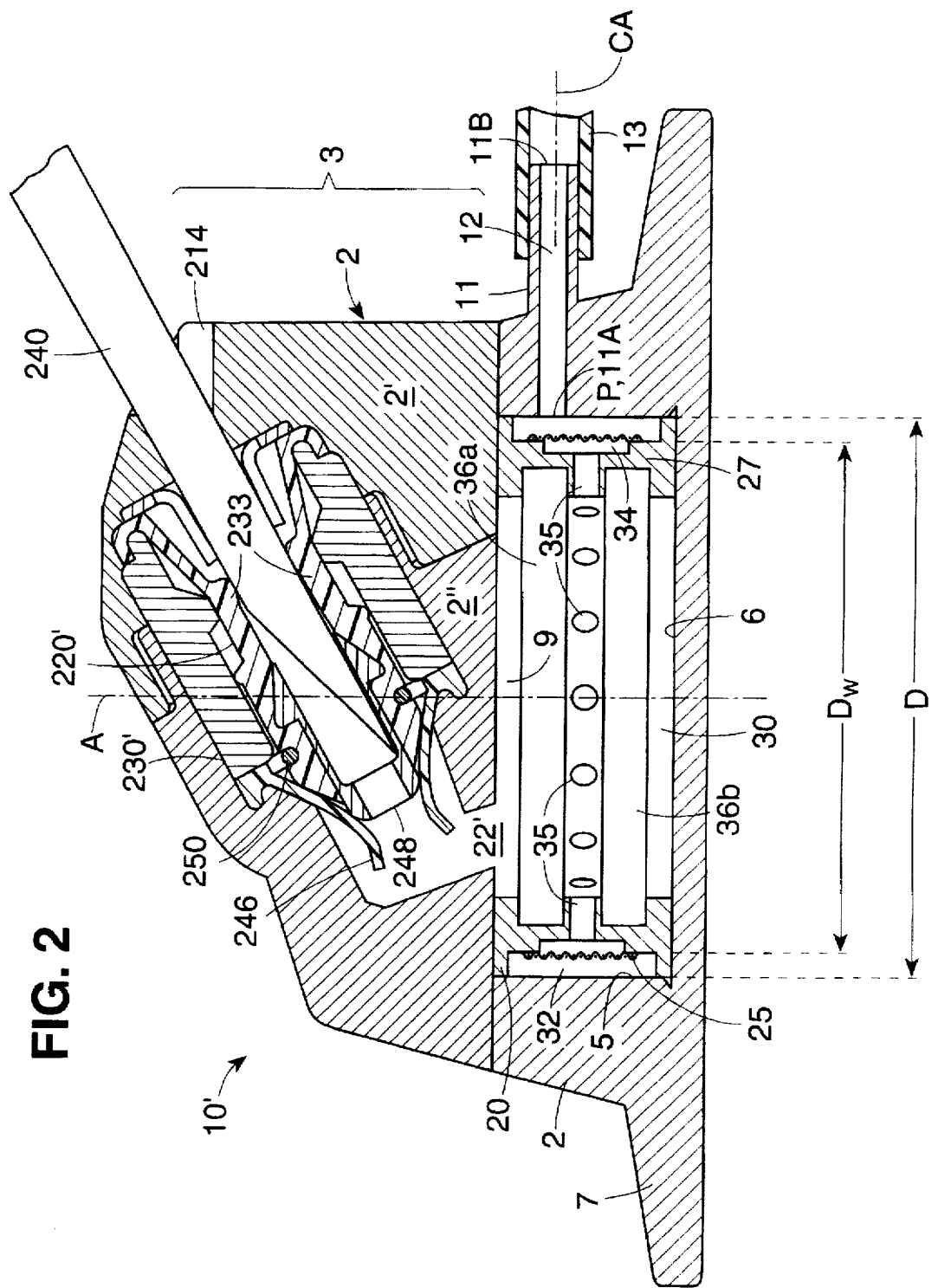
FIG. 2 shows in sectional schematic form, an implantable two-stage filter access device of the invention with an internal reservoir and filter assembly with a valve embodiment comprising a duck bill type valve.

The device 10 of the present invention as depicted in FIGS. 1A, 1B, and 2, includes a biocompatible housing 2 having a radially extending base flange plate 7. For ease of manufacture, housing 2 may be comprised of several parts, e.g., part 2', part 2", and part 2"'. The housing 2 includes an interior reservoir 9 principally disposed in part 2"' defined by lateral surface 5 and bottom surface 6. As shown, reservoir 9 is cylindrical (having diameter D), extending along central axis A, with a circular cross-section perpendicular to central axis A. In other embodiments, reservoir 9 may be "substantially cylindrical", including functionally equivalent geometries, such as having an elliptical or polygonal cross-section perpendicular to central axis A. Flange plate 7 may include a multiplicity of apertures through which sutures may pass to anchor the device to the patient's muscle fascia. The parts 2' and 2" include a septumless access port and valve/seal assembly 3 which is coupled to an aperture 22'.

The reservoir 9 is in fluid communication with aperture 22' of the access port and valve/seal assembly 3. Part 2"' includes an outlet P from which an outlet cannula 11 extends. In the illustrated embodiment, cannula 11 extends from part 2"" at a first end 11A (where it is integral with part 2"' at outlet P) to a second end 11B which receives a catheter 13.

FIGS. 1A, 1B, and 2 show a two-stage filter assembly 20 installed within reservoir 9. Also shown in the figures is the lateral surface 5 of the reservoir 9. As shown in the figures, filter assembly 20 comprises a fluid permeable first wall 25 (stage 1) and a fluid permeable second wall 27 (stage 2). First wall 25 is substantially cylindrical and has a diameter $D_w$, which is less than D. That wall 25 is fluid permeable and is located interior to and spaced apart from the lateral surface 5 of reservoir 9 to allow a full 360° of fluid flow through the first annular chamber 32 established between first wall 25 and lateral surface 5. First wall 25 also establishes a first reservoir chamber 30 interior to first wall 25. In the embodiment of FIGS. 1A, 1B, and 2, chamber 30 houses second wall 27 which divides that chamber 30 to form second annular chamber 34 on one side of wall 27, with the remainder of chamber 30 on the other side of, and interior to, wall 27, as described in detail below.

The first annular chamber 32 and the first reservoir chamber 30 (as a whole) are in fluid communication only through first wall 25. In accordance with the invention, first wall 25, as shown in FIGS. 1A, 1B, and 2, functions to remove particulate material from fluid injected into first reservoir chamber 30 prior to entry of that fluid into chamber 32 and eventually into internal channel 12 within and defined by outlet cannula 11. Internal channel 12 extends from the first end 11A of outlet cannula 11 along a channel axis CA from points on the lateral surface 5 of reservoir 9, to the second end 11B of outlet cannula 11. In accordance with the invention, channel 12 is in direct fluid communication only with first annular chamber 32.

The structure of first wall 25 may be selected to produce desired filtering capability. For example, first wall 25 may be formed from a mesh screen, the porosity of which may also be varied to achieve desired filtering and fluid flow rates. In the various forms of the invention different mesh sizes may be used, or alternatively, different forms of filter material may be used.

As shown in FIGS. 1 and 2, second wall 27 is also "substantially cylindrical" and fluid permeable, being placed interior to and spaced apart from first wall 25, establishing a second annular chamber 34 within first reservoir chamber 30 and between first wall 25 and second wall 27. Second annular chamber 34 provides the only fluid flow paths between the first central portion (i.e., along central axis A) of reservoir chamber 30 and first annular chamber 32. Second wall 27 allows 360° of fluid flow through that wall 27 to chamber 32. In accordance with the present invention, second wall 27 may take the form of a toroidal substrate extending about central axis A, and having a plurality of radially extending apertures 35 extending therethrough (and providing the fluid flow paths). The apertures 35 provide filtering, removing particulate material that is too large to pass therethrough. The number and size of apertures 35 is selected to provide desired filtering and flow rates. In the embodiment of FIGS. 1 and 2, the substrate also supports first wall 25, which is affixed to that substrate.

In the embodiment of FIGS. 1A, 1B and 2, second wall 27 is shaped to create an upper cylindrical reservoir sub-chamber 36a and a lower cylindrical reservoir sub-chamber 36b, respectively, within first reservoir chamber 30. The right-circular cylindrical geometry of those reservoir sub-chambers provides sharp right angle corners within first reservoir chamber 30. During the injection of fluid into the port through passageway 22', accumulation of particulate material or other debris in those corners is promoted and, in some cases, particulate material and other debris is held in those corners by eddy currents.

Additional embodiments of the filter assembly of the device of the present invention, including both single and double stage filters, are described more fully in U.S. patent application Ser. No. 08/472,544, "Implantable Treatment Material Device", filed on even date herewith and incorporated herein by reference.

With particular reference to the access port and valve/seal assembly 3, parts 2' and 2" include an elongated open guidance channel 214 communicating with the entry port 216 of the housing. The guidance channel may be of a generally V-shaped configuration, but other configurations such as U-shaped configurations are suitable. Housing 2 may contain a plurality of guidance channels. The open guidance channel allows for an increased strike area for guiding a filament into the entry port of the device.

As shown in FIG. 1B, device 10 may be accessed by inserting a filament 240, such as a cannulated needle, into elastomeric member 220 positioned within a housing insert 230 which is disposed in passageway 222. Housing insert 230 is employed for ease of manufacture, but it should be understood that it could also be integral in the geometry of housing 2. Elastomeric member 220, in this embodiment, includes a plug 226 and an opening 242, terminating in a cap 224. Cap 224 may be titanium, stainless steel or any other suitable resilient metal. Elastomeric member 220 farther has a transition region 232 along which the outer diameter of the elastomeric member 220 decreases from a first larger diameter to a second smaller diameter.

The interaction between the elastomeric member 220, specifically its transition region 232, and the housing insert 230 will create a seal around an accessing filament. Elastomeric member 220 has a substantially thinner walled section 234 above transition region 232. Also within passageway 222 is a filament retention piece 236. Valve opening 242 in part 2" is in fluid communication with internal reservoir 9 through aperture 22'. Plug 226 is located at the distal end of the elastomeric member 220 in a sealing engagement with passageway 222. FIG. 1A shows valve opening 242 in a closed configuration, and FIG. 1B shows valve opening 242 in an open configuration.

Typically the filament 240 would be a needle but a catheter or other substantially rigid member could be used. Before movement of plug 226 out of passageway 222 and the opening of valve means opening 242 which would allow communication between filament 240 and aperture 22', a seal 233 is first created about filament 240. Seal 233 is maintained at all times when plug 226 and valve means opening 242 allow communication between the filament 240 and aperture 22', and the seal is released only after plug 226 returns to a sealing engagement within passageway 222. Seal 233 is generated when the transition region 232 of elastomeric member 220 is pulled into the smaller diameter of housing insert element 230, compressing the elastomeric member 220 against the accessing filament 240. The filament retention piece 236 is configured with an inner dimension smaller than the outer dimension of the accessing filament 240, such that as the accessing filament 240 is introduced into the entry port of the device, the filament retention piece 236 expands and applies a force against the accessing filament 240 to resist its withdrawal from the entry port. Filament retention piece 236 may employ a strain release slot or slots 237 to tune the force applied to accessing filament 240 and increase its useful life span.

FIG. 2 depicts device 10' which includes another embodiment of the valve of the present invention. The valve of this embodiment is a duck bill valve 246 in place of plug 226 and valve opening 242. Cap 248 has replaced cap 224. A fastener 250 assists in maintaining the coupling between elastomeric member 220' and cap 248. Elastomeric member 220' has all of the attributes of elastomeric member 220. Housing insert 230' is substantially like housing insert 230, and the remaining structural elements of this valve means embodiment are similar to those described in relation to FIGS. 1A and 1B. Accessing filament 240 moves cap 248 and elastomeric element 220' to create a seal 233 about filament 240 before valve 246 is opened. As filament 240 advances, cap 248 moves to open valve 246 to establish fluid communication between the filament and internal reservoir 9. Seal 233 is maintained about the accessing filament during the time that the valve is open, and seal 233 is not released until after the valve is closed. FIG. 2 depicts the duck bill valve in its open configuration.

Additional embodiments of septumless valves suitable for use in the present invention are disclosed in the specification and drawings of U.S. patent application Ser. No. 08/390,014, filed Feb. 17, 1995 and entitled "Implantable Access Device", incorporated herein by reference.

In other forms of the invention, one or more access devices with internal filter assemblies of the type described above may also be functional components of an infusate pump apparatus, such as that disclosed in U.S. Pat. No. 4,496,343, incorporated herein by reference. In this embodiment, the filter assembly may be contained within a common housing, or the infusate pump apparatus and the side access port may be connected but not contained within a common housing, as discussed in detail in the above-referenced U.S. patent application Ser. No. 08/472,544 ("Implantable Treatment Material Device", and in U.S. patent application Ser. No. 08/390,014 "Implantable Access Device."

The invention has been described above in terms of a biocompatible housing having the specific resealable septumless entry port disclosed in U.S. patent application Ser. No. 08/390,014. However, the subject invention can also be embodied using other septumless entry ports, such as those disclosed in U.S. Pat. Nos. 5,356,381, 5,350,360, 5,281,199, 5,263,930, 5,266,879, 5,180,365, 5,057,084, 5,053,013, as well as others.

Those of skill in the art will recognize that the invention may be embodied in other specific forms without departing from the spirit or essential characteristics thereof. The presently described embodiments are therefore to be considered in all respects as illustrative and not restrictive, the scope of the invention being indicated by the appended claims rather than by the foregoing description, and all variations of the invention which are encompassed within the meaning and range of equivalency of the claims are therefore intended to be embraced therein.

What is claimed is:

1. An implantable access device comprising:
   A. a biocompatible housing having at least one entry port and at least one aperture with a passageway extending therebetween, said entry port being adapted to receive a filament for passage into said passageway, said housing further including and disposed in said passageway a valve assembly comprising a valve and a sealing element, said valve assembly adapted to be activated by said filament after passage of said filament through said entry port whereupon a seal, independent of activation of said valve, is created by said sealing element about said filament before said valve opens to allow access through said passageway, said aperture communicating with an internal substantially cylindrical reservoir in the housing, said reservoir being defined by a lateral surface extending about a central axis and a bottom surface;
   B. an outlet extending through said housing along an outlet channel axis from a point on said lateral surface of said reservoir, and
   C. a filter assembly disposed in said reservoir, said filter assembly including a substantially cylindrical fluid permeable first wall interior to and spaced apart from said lateral surface of said reservoir, said first wall establishing a first annular chamber between said first wall and said lateral surface and a first reservoir chamber interior to said first wall, said first annular chamber and said first reservoir chamber being in fluid communication only through said first wall, and said outlet being in direct fluid communication with said first annular chamber.

2. The implantable access device according to claim 1 further comprising a cannula extending at a first end thereof from said outlet and having a second end thereof adapted to receive a catheter, said outlet cannula further defining an internal channel extending from said first end, along said channel axis to said second end.

3. The implantable access device according to claim 1, wherein said filter assembly further includes:
   a substantially cylindrical fluid permeable second wall interior to and spaced apart from said first wall, said second wall establishing within said first reservoir chamber:
   i. a second annular chamber between said second wall and said first wall; and
   ii. at least one reservoir sub-chamber interior to said second wall;
   said second annular chamber being in fluid communication with said reservoir sub-chamber only through said second wall and being in fluid communication with said first annular chamber only through said first wall.

4. The implantable access device according to claim 3 wherein said filter assembly includes a substrate extending about said central axis, said substrate forming said second wall and supporting said first wall.

5. The implantable access device according to claim 4, wherein said substrate is a rigid material and said second wall is formed by said substrate, said second wall having a plurality of passages extending therethrough.

6. The implantable access device according to claim 4, wherein said filter assembly further comprises a second reservoir sub-chamber interior to said second wall and adjacent to the bottom surface of the reservoir.

7. The implantable access device according to claim 6, wherein said substrate is a rigid material and said second wall is formed by said substrate, said second substrate having a plurality of passages extending radially therethrough.

8. The implantable access device according to claim 6, wherein said reservoir sub-chambers comprise one or more acute corners in their defining surfaces.

9. The implantable access device according to claim 3, wherein said reservoir sub-chamber is defined by surfaces that establish a principal fluid flow path extending in said reservoir sub-chamber and through said second wall, and establish one or more eddy flow paths that are substantially within said reservoir sub-chamber.

10. The implantable access device according to claim 3, wherein said reservoir sub-chamber is substantially cylindrical.

11. The device according to claim 1 wherein said valve comprises a miter valve.

12. The device according to claim 1 wherein said valve comprises a plug seated in sealing engagement within said passageway, said plug adapted to be opened by forcing said plug from said sealing engagement by movement of said filament through said passageway.

13. The device according to claim 1 wherein said valve comprises an opening adapted to be opened by movement of said filament into said valve assembly.

14. The device according to claim 1 wherein said outlet is adapted to be connected to a catheter, a graft, or an implanted medical device.

15. The device according to claim 1 wherein said filament is a needle having a point and wherein said housing further includes means for guiding said needle into said entry port.

16. The implantable access device of claim 1, further comprising an infusion pump apparatus, said infusion pump apparatus including an input, an output and a pump for selectively driving fluid entering said input to exit said output, and coupling means for coupling at least one of said input and said output of said pump apparatus to said implantable access device.

17. The implantable access device of claim 16, wherein said coupling means includes means for coupling said outlet port of said implantable access device to said input of said infusion pump apparatus.

18. The implantable access device of claim 16, wherein said implantable access device and said infusion pump apparatus are contained within a common housing.

* * * * *